(12) United States Patent
Wagner

(10) Patent No.: US 11,559,475 B2
(45) Date of Patent: *Jan. 24, 2023

(54) HAIR STRENGTHENING INGREDIENT AND METHOD FOR STRENGTHENING HAIR

(71) Applicant: LIW PATENT COMPANY LIMITED BY GUARANTEE, Dublin (IE)

(72) Inventor: Sabine Wagner, Sydney (AU)

(73) Assignee: LIW PATENT COMPANY LIMITED BY GUARANTEE, Dublin (IE)

( * ) Notice: Subject to any disclaimer, the term of this patent is extended or adjusted under 35 U.S.C. 154(b) by 404 days.

This patent is subject to a terminal disclaimer.

(21) Appl. No.: 16/302,877

(22) PCT Filed: Feb. 13, 2017

(86) PCT No.: PCT/CN2017/073361
§ 371 (c)(1),
(2) Date: Nov. 19, 2018

(87) PCT Pub. No.: WO2017/197931
PCT Pub. Date: Nov. 23, 2017

(65) Prior Publication Data
US 2020/0315936 A1     Oct. 8, 2020

(30) Foreign Application Priority Data
May 19, 2016 (CN) .......................... 201610338449.8

(51) Int. Cl.
| | | |
|---|---|---|
| *A61K 8/41* | (2006.01) | |
| *A61K 8/24* | (2006.01) | |
| *A61K 8/31* | (2006.01) | |
| *A61K 8/34* | (2006.01) | |
| *A61K 8/362* | (2006.01) | |
| *A61K 8/365* | (2006.01) | |

(Continued)

(52) U.S. Cl.
CPC .................. *A61K 8/41* (2013.01); *A61K 8/24* (2013.01); *A61K 8/31* (2013.01); *A61K 8/347* (2013.01); *A61K 8/362* (2013.01); *A61K 8/365* (2013.01); *A61K 8/46* (2013.01); *A61K 8/585* (2013.01); *A61K 8/891* (2013.01); *A61Q 5/002* (2013.01); *A61Q 5/12* (2013.01); *A61K 2800/884* (2013.01)

(58) Field of Classification Search
CPC .... A61K 8/362; A61K 8/41; A61K 2800/884; A61K 8/365; A61K 8/24; A61K 8/31; A61K 8/342; A61K 8/347; A61K 8/46; A61K 8/585; A61K 8/891; A61K 2800/882; A61K 2800/95; A61K 8/4913; A61K 2800/94; A61K 8/22; A61K 8/40; A61K 8/4926; A61K 8/4973; A61K 2800/30; A61K 2800/42; A61K 2800/51; A61K 2800/596; A61K 2800/70; A61K 2800/81; A61K 8/0204; A61K 8/0216; A61K 8/33; A61K 8/345; A61K 8/35; A61K 8/36; A61K 8/416; A61K 8/42; A61K 8/445; A61K 8/447; A61K 8/45; A61K 8/498; A61K 8/60; A61K 8/44; A61K 2800/412; A61K 2800/5426; A61K 2800/594; A61K 288/88; A61K 8/023; A61K 8/11; A61K 8/19; A61K 8/20; A61K 8/23; A61K 8/361; A61K 8/418; A61K 8/69; A61K 8/731; A61K 8/732; A61K 8/8147; A61K 8/8152; A61K 8/8158; A61K 8/8182; A61K 8/84; A61K 8/86; A61K 8/9229; A61K 9/0017; A61K 9/1635; A61K 9/1694; A61Q 5/002; A61Q 5/10; A61Q 5/12; A61Q 5/00; A61Q 5/06; A61Q 5/08; A61Q 5/02; A61Q 5/04; A61Q 5/004; A61Q 17/04; A61Q 19/007; A61Q 19/10; A61Q 5/065; A61Q 17/02; A61Q 19/00; A45D 7/04; A45D 7/06; A45D 2007/001; C07C 1/20; C07C 11/04; C07C 11/06; C07C 2531/14
See application file for complete search history.

(56) References Cited

U.S. PATENT DOCUMENTS

| | | |
|---|---|---|
| 5,487,884 A | 1/1996 | Bissett et al. |
| 9,095,518 B2 | 8/2015 | Pressly et al. |

(Continued)

FOREIGN PATENT DOCUMENTS

| | | | | |
|---|---|---|---|---|
| CN | 105267066 | * | 1/2016 | ............... A61K 8/92 |
| CN | 105267066 A | | 1/2016 | |

(Continued)

OTHER PUBLICATIONS

CN 105267066 translation (Year: 2016).*

(Continued)

*Primary Examiner* — Audrea B Coniglio
(74) *Attorney, Agent, or Firm* — Curatolo Sidoti & Trillis Co., LPA; Salvatore A. Sidoti; Brittany L. Kulwicki

(57) ABSTRACT

A method for strengthening and repairing keratin fibres including providing a first—and a second crosslinking composition, wherein the first—crosslinking composition comprises an at least bi-functional Brønsted-base and the second—crosslinking composition comprises—an at least bi-functional organic acid, and a cosmetically acceptable carrier; applying the first—as well as the second—crosslinking composition to keratin fibres; and optionally mixing the first—crosslinking composition into a commercially available hair coloring or hair bleaching composition.

30 Claims, No Drawings

(51) Int. Cl.
- *A61K 8/46* (2006.01)
- *A61K 8/58* (2006.01)
- *A61K 8/891* (2006.01)
- *A61Q 5/00* (2006.01)
- *A61Q 5/12* (2006.01)

(56) References Cited

U.S. PATENT DOCUMENTS

| | | | |
|---|---|---|---|
| 2011/0155167 A1* | 6/2011 | Deconinck | A61K 8/41 132/208 |
| 2015/0034117 A1* | 2/2015 | Pressly | A61K 8/365 132/202 |
| 2015/0034119 A1 | 2/2015 | Pressly et al. | |
| 2015/0037270 A1 | 2/2015 | Pressly et al. | |
| 2015/0037271 A1 | 2/2015 | Pressly et al. | |
| 2015/0174023 A1 | 6/2015 | Washington et al. | |

FOREIGN PATENT DOCUMENTS

| | | |
|---|---|---|
| CN | 105496804 A | 4/2016 |
| CN | 105902403 A | 8/2016 |
| CN | 106265109 A | 1/2017 |
| DE | 100 51 774 A1 | 4/2002 |
| EP | 0 234 261 A1 | 9/1987 |
| EP | 2 090 295 A1 | 8/2009 |
| WO | 91/16034 A1 | 10/1991 |
| WO | 91/16035 A1 | 10/1991 |
| WO | 2012/027369 A2 | 3/2012 |
| WO | 2015/017768 A1 | 2/2015 |

OTHER PUBLICATIONS

International Search Report and Written Opinion Form PCT/ISA/210 and PCT/ISA/237, International Application No. PCT/CN2017/073361, pp. 1-11, International Filing Date Feb. 13, 2017, dated May 12, 2017.

Brooks, G., et al. "Treatment Regimens for "Styled" Black Hair" Ethnic Product Development Seminar Paper, Cosmetics & Toiletries 98:59-68 (May 1983) cited in Specification.

W. Fassbender, Parfumerie & Kosmetik :Aminosäuresole in der modemen Kosmetik 39 (1) S. 11-16 (1958), with English translation "Amino acid sols in modern cosmetics" cited in Specification.

CTFA International Cosmetics Ingredient Dictionary and Handbook "Hair Fixatives" 12th edition (2008) pp. 3201-3202 cited in Specification.

* cited by examiner

HAIR STRENGTHENING INGREDIENT AND METHOD FOR STRENGTHENING HAIR

CROSS-REFERENCES TO RELATED APPLICATIONS

This application is the U.S. National Phase Entry of PCT Application No. PCT/CN2017/073361 filed on Feb. 13, 2017, which claims priority to Chinese patent application No. 201610338449.8, filed on May 19, 2016, the entire disclosure of each of which is incorporated herein by reference.

FIELD OF THE INVENTION

A method, composition and kit for strengthening hair including providing a composition capable of crosslinking the Amino-acid groups of keratin fibers, comprising also the mixing of such crosslinking composition with commercially available hair color or hair bleaching formulations.

BACKGROUND OF THE INVENTION

The invention is related to hair treatment agent, which have bi-functional active ingredients, wherein the active ingredients react with the amine groups of the hair and thereby improve the quality of the hair in various ways, and significantly increase the durability of permanent waves. The current invention is also related to a method for improving the condition of the hair.

Constant bleach, permanent waves and coloration, and sometimes even frequent hair wash with degreasing surfactants or other active ingredients can result in damages of the hair structure. The hair turns brittle and loses its luster. In addition, combing the hair charges the hair electrostatically and the roughened surface of the hair leads to entanglement of the hairs. Combing will thus become more difficult.

Hair treatment agents with an nourishing effect of the hair and which can facilitate hair combing have therefore become important and were known in the European patent application EP 234261. Such agents are, for instance, in the form of clear hair care rinsing solution or in the form of so called "cream-rinses" emulsion distributed on the still wet hair after hair wash, left on the hair for a couple of minutes to an hour and the hair are then rinsed with water.

Hair treatment agents on the basis of the above mentioned conditioning active ingredients, however, only show satisfactory results when treating dry and spongy hair. For the treatment of easily greasy hair, they tend to be less satisfactory, since their application makes the hair greasier so that the durability of the hair style decreases. It is also known that the durability of the hair style is dependent on the disulfide bonds, which are unstable and can be easily reduced to sulfhydryl groups under reducing condition. There have been plenty attempts to reestablish the disulfide bonds through the introduction of oxidizing agents. A lot of agents which improve the stability of the permanent waves are based on such technology. Also a great number of patents and patent applications are directed to reestablishment of disulfide bonds, such as the U.S. Pat. No. 9,095,518 B2, the US patent applications 2015034119 A1, 201537270 A1, 201537271 A1 and WO 2015017768 A1. Nevertheless, the hair treatment agents which are described in these documents have lots of room for improvements.

It has also been attempted to apply amino acids, such as a weak acid mixture of different amino acids and vitamins (US-PS 4201235), as a hair conditioning component to avoid the disadvantages of the known hair treatment agents. However, the production of such a mixture of different vitamins and amino acids is troublesome and expensive.

Furthermore, the application of keratin-hydrolyzate and citric acid in a "neutralizing shampoo" is known from the literature "Cosmetics and Toileteries" Vol 98 (1983), S. 59-68. This shampoo, however, possesses only a low hair care effect and leads to a strong dehydration of the hair. For this reason, it is necessary to apply once or repeatedly hair conditioning agents after hair wash.

It is also known from the literature W. Fassbender, Parfümerie & Kosmetik, 39 (1), S. 11-16 (1958) that the amino acid liquid, which contains 18 to 22 different amino acids, can be applied, for example, in weak acid adjusted hair treatment and hair care agent. The production of such amino acid liquid is carried out by fractionated hydrolysis of natural proteins and subsequent purification of the hydorlyzates obtained. It is therefore difficult to guarantee the constant composition of the liquid, which is important for the quality of the cosmetic agent.

The object of the invention is to provide a hair treatment agent and a hair treatment method which are based on bi-functional organic acids as well as bi-functional Brønsted bases and which overcome the above described disadvantages. It is also an objective of the present invention to provide such hair treatment method at an acidic pH to improve the hair feel after such treatment is provided. The current invention provides especially a novel hair treatment agent, which is suitable for producing long-lasting hair styles. It has been surprisingly found that the hair treatment agent containing the following combination meets these requirements:

a: a first formula, comprising an at least bi-functional Brønsted-base of the general formula X—R—Y, wherein X and Y are proton-acceptor groups and R is an organic spacer comprising 1 to 20 carbon atoms, and 0 to 5 oxygen atoms, and 0 to 5 nitrogen atoms, and X—R—Y having a molecular weight of less than 500 g/mol (1. Step), and b: a second formula, comprising an at least a bi-functional, physiologically compatible organic acid—which can react with the amine groups of the hair (2. Step), characterized in that the first formula and the second formula both have a pH of 1.5 to 7.

In both of these two formulations, the at least bi-functional Brønsted-base as well as the at least bi-functional organic acid have a concentration of 0.01-30% by weight respectively. To adjust the pH values of the first and the second formula, organic as well as inorganic acids and bases can be used. Those pH adjusting agents can be monofunctional or polyfunctional.

In general, formula (a) is applied before formula (b). However, it is also possible to apply formula (b) before formula (a).

The proton-acceptor groups X and Y of the at least bi-functional Brønsted-base of step (a) are independently selected from the group of carboxylate, nitrate, hydrogen phosphate, phosphate, primary amine, secondary amine, tertiary amine, sulphate, and carbonate.

The at least bi-functional organic acid of step (b) is selected from the group of Oxalic-, Malonic-, Succinic-, Glutaric-, Adipic-, Pimeric-, Suberic-, Azelaic-, Sebacic-, Undecanedioic-, Dodecanedioic-, Methylmalonic-, Methyl succinic-, 2-Methylglutaric-, Aspartic-, Maleic-, Fumaric-, Itaconic-, Mesaconic-, Methylmaleic-, Phthalic-, Isophthalic-, Terephthalic-, Malic-, Ketomalonic-, 4-Ketopimelic-, Citric-, Isocitric-, Actonitic-, Propane-1,2,3-tricarboxylic-, Trimesic-, Methanetetracarboxylic-, Ethylenetetracarboxylic-, Meso-butane-1,2,3,4-tetracarboxylic-, Furantetracarboxylic-acid, derivatives and mixtures thereof.

The hair can be dried inbetween the application of steps (a) and (b) and the drying time is 1 to 60 minutes, wherein a drying device is used for drying the hair.

These formulae should be left on the hair for 1 to 45 minutes.

It is of advantage that the formulae of steps (a) and (b) are independently mixed into a cosmetically acceptable carrier and where the cosmetically acceptable carrier of the formula of step (a) is either identical or not to the cosmetically acceptable carrier of the formula of step (b).

It is also of advantage that the formula of step (a) is mixed into a commercially available hair coloring or hair bleaching formulation prior to the application to hair. The formula of step (b) can also be mixed with a commercially available hair coloring or hair bleaching formulation in case the application steps are inverted.

It is also advisable that prior to the application of step (a) the hair is treated with a thioglycolic acid containing hair care composition for permanent wave treatment.

SUMMARY OF THE INVENTION

Described herein is a method for strengthening and/or repairing hair comprising the steps of: (a) applying a hair care composition to hair, wherein the hair care composition comprises an at least bi-functional Brønsted-base of the general formula X—R—Y, wherein X and Y are proton-acceptor groups and R is an organic spacer comprising 1 to 20 carbon atoms, and 0 to 5 oxygen atoms, and 0 to 5 nitrogen atoms, and X—R—Y having a molecular weight of less than 500 g/mol, and leaving the—hair strengthening composition on for 1 to 45 minutes, (b) optionally rinsing, shampoo'ing and/or drying the hair drying, (c) applying to the hair a formula comprising a crosslinking composition comprising an at least bi-functional organic acid capable of reacting with the amine groups of the hair, and leaving the—hair strengthening composition on for 1 to 45 minutes, (d) optionally rinsing, shampoo'ing and/or drying the hair, characterized in that the first formula and the second formula both have a pH of 1.5 to 7.

Optionally, the hair strengthening composition of step (a) can be mixed into commercially available hair coloring or hair bleaching formulations prior to the application. Alternatively, the formula of step (c) is mixed into a commercially available hair coloring or hair bleaching formulation prior to the application to hair. When applied without prior mixing into either a commercially available hair coloring or bleaching formulation the hair strengthening method can be altered such that the hair strengthening composition of step (c) is applied before hair strengthening composition of step (a) is.

DETAILED DESCRIPTION OF THE INVENTION

In this document, including in all embodiments of all aspects of the present invention, the following definitions apply unless specifically stated otherwise. All percentages are by weight of the total composition. All ratios are weight ratios. References to 'parts' e.g. a mixture of 1 part X and 3 parts Y, is a ratio by weight. "QS" or "QSP" means sufficient quantity for 100% or for 100 g.+/−indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 25° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer. Herein: "min" means "minute" or "minutes"; "mol" means mole; "nanometers" is abbreviated "nm"; "g" following a number means "gram" or "grams". All weights as they pertain to listed ingredients are based on the active level and do not include carriers or by-products that may be included in commercially available materials. Herein, "comprising" means that other steps and other ingredients can be in addition. The compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In at least one embodiment" means that one or more embodiments, optionally all embodiments or a large subset of embodiments, of the present invention has/have the subsequently described feature. Where amount ranges are given, these are to be understood as being the total amount of said ingredient in the composition, or where more than one species fall within the scope of the ingredient definition, the total amount of all ingredients fitting that definition, in the composition. For example, if the composition comprises from about 1% to about 5% fatty alcohol, then a composition comprising 2% stearyl alcohol and 1% cetyl alcohol, would fall within the scope.

"Viscosity" is measured at 25° C. using a HAAKE Rotation Viscometer VT 550 with cooling/heating vessel and sensor systems according to DIN 53019 at a shear rate of 12.9 s$^{-1}$.

"Water-soluble" refers to any material that is sufficiently soluble in water to form a clear solution to the naked eye at a concentration of 0.1% by weight of the material in water at 25° C. The term "water-insoluble" refers to any material that is not "water-soluble".

"Substantially free from" or "substantially free of" means less than about 1%, or less than 0.8%, or less than 0.5%, or less than 0.3%, or about 0%, by total weight of the composition or formulation.

"Keratin fibres" means fibrous material composed of keratin. "Hair" means mammalian keratin fibres including scalp hair, facial hair, eyelashes, and body hair. It includes such hair still being attached to a living subject and also hair that has been removed therefrom such as hair swatches and hair on a doll/mannequin. In at least one embodiment, "hair" means human hair. "Hair shaft" or "hair fibre" means an individual hair strand and may be used interchangeably with the term "hair."

"Cosmetically acceptable" means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives" includes but is not limited to, amide, ether, ester, amino, carboxyl, acetyl, acid, salt and/or alcohol derivatives of a given compound. In at least one embodiment, "derivatives thereof" means the amide, ether, ester, amino, carboxyl, acetyl, acid, salt and alcohol derivatives.

"Monomer" means a discrete, non-polymerized chemical moiety capable of undergoing polymerization in the presence of an initiator or any suitable reaction that creates a macromolecule e.g. such as polycondensation, polyaddition, anionic or cationic polymerization. "Unit" means a monomer that has already been polymerized i.e. is part of a polymer.

"Polymer" means a chemical formed from the polymerization of two or more monomers. The term "polymer" shall include all materials made by the polymerization of monomers as well as natural polymers. Polymers made from only one type of monomer are called homopolymers. Herein, a polymer comprises at least two monomers. Polymers made from two or more different types of monomers are called copolymers. The distribution of the different monomers can be random, alternating or block-wise (i.e. block copolymer). The term "polymer" used herein includes any type of polymer including homopolymers and copolymers.

"Kit" means a package comprising a plurality of components. "Kit" may be referred to as "kit-of-parts". An example of a kit is, for example, a first composition and a separately packaged second composition and optionally application instructions.

The details of the different aspects of the invention are described hereinafter.

Description

Described herein is a method for strengthening keratin fibres while at the same time providing excellent hair feel properties of the treated hair. The method allows the achievement of a semi-permanent strengthening of the hair shaft combined with excellent hair feel properties either upon treatment of the hair with such hair strengthening composition or upon mixing of the hair strengthening composition with commercially available hair coloring or bleaching compositions. The method comprises two—formulations—which—both have a pH value of—<7. The hair strengthening effect is retained after at least one shampoo treatment. In addition, the inventors have found that this method increases the water- and humidity-resistance of the shape, increases the ease of style and/or increases the manageability of the shape—.

Without wishing to be bound by any theory, it is believed that the above benefits are due to the steps conducted, their sequence, as well as the specific components used including the active agent. It is believed that the selected active agents of the first—formula diffuse into the shaft of the keratin fibre, react with carboxylic acid—groups in the keratin polypeptide and crosslink these functional groups in the keratin protein structure, providing sufficient crosslinks to overcome the innate restoring force of the keratin fibre structure. The first—formulation cannot react with potentially available sulfhydrol groups of the hair as the reaction conditions are acidic. A hypothetical reaction of potential sulfhydrol groups of the hair requires de-protonation of such sulfhydrol groups. As the selected protonating agents of the present invention are stronger acids than sulfyhydrol groups are, such reaction cannot occur. It is also believed that the selected active agents of the second—formula diffuse into the shaft of the keratin fibre, react with the amine—groups in the keratin polypeptide and crosslink these functional groups. This results in a durable strengthening of keratin fibres, for example a durable hair damage repair. As the pH value of the first as well as the second formulation is pH<7, hair-swelling in the alkaline pH region is avoided. Hair-swelling in the alkaline leads to the hair cuticular opening and extending away from the hair shaft which is commonly noticed as an increase in hair roughness, and is therefore undesired.

The details of the different aspects of the invention are described hereinafter.

Crosslinking Composition

The crosslinking compositions of the present invention—work synergistically. The order in which they are applied is irrelevant for the benefit to be achieved-. To achieve the desired hair strengthening effect in combination with excellent hair feel properties it is important that both composition have a pH of 1.5 to 7. Applying alkaline composition to hair leads the hair to swell. Upon swelling, the hair cuticles lift and extend away from the hair shaft causing a rough hair feel, reduced hair smoothness and less hair shine as hair fibers do not align and therefore do not provide a uniform surface to reflect light. Applying hair strengthening formulation as per the current invention minimizes the need to formulate additional hair smoothening actives into such hair care formulation which are often perceived as heavy, greasy and unnatural.

When mixed with commercially available hair coloring or hair bleaching formulation the mixed formula is applied first followed by the second, not mixed, hair strengthening composition. A dwell time of 1-45 minutes between the application steps is advisable. Optionally, the hair is rinsed and dried between the first and the second application step. Optionally, a 1-45 minutes waiting time is employed inbetween the application of the acidic and caustic hair strengthening composition.

The Second—Hair Strengthening Composition [b] is Typically Applied after the First Hair Strengthening Composition [a] and Comprises at Least Bi-Functional Brønsted-Acids as Crosslinking Agents. At Least Bi-Functional Brønsted-Acids are Preferred for the Acidic Hair Strengthening Composition as they can Bridge Between Neighbored Amino-Groups of the Hair. Most bi-functional Brønsted-acids are naturally-derived which is preferred by consumers versus synthetic compounds. This is not only for perceived health and lack of sensitization reasons, but also for sustainability and environmental reasons as naturally-derived compounds break down naturally and quickly and do not require special disposal methods. Furthermore, those are also easy to source and relatively inexpensive.

Without wishing to be bound by theory, the agent of the first—hair strengthening composition react with the carboxylic acid groups of the hair and provide further crosslinks of the hair proteins. The hair comprises polypeptides of keratin having carboxylic acid functional groups [—COOH], hydroxyl- [—OH], amino- [—NH$_2$], and potential some sulfhydrol [—SH] groups. Different active agents can react preferentially with each functional group. For instance, at least bi-functional Brønsted-acids react with amino groups whereas at least bi-functional proton acceptors react with carboxylic acid groups.

The at least bi-functional Brønsted-acid as well as the at least bi-functional proton acceptor is present in a concentration of 0.01 to 30% by weight of the total—composition, preferably from 0.1- to 30-%, more preferably from 0.5- to 2-5%, even more preferably from 1 to 20-%, and most preferably from 2 to 15% and most preferably from 3 to -10%. —In at least one embodiment, the first—as well as the second—crosslinking composition independently comprise a cosmetically acceptable carrier. In at least one embodiment, the cosmetically acceptable carrier is any carrier suitable for formulating the active agent into a crosslinking composition being suitable for application onto hair. In at least one embodiment, the cosmetically acceptable carrier is selected from either an aqueous medium or an aqueous-alcoholic medium. In at least one embodiment, when the carrier is an aqueous-alcoholic carrier, this carrier comprises water and an alcohol. In at least one embodiment, the alcohol is selected from the group consisting of: ethanol, isopropanol, propanol, and mixtures thereof. In at least one embodiment, when the carrier is an aqueous carrier, this carrier consists essentially of water and is substantially free of alcohol. In at least one embodiment, the first—as well as the second—crosslinking composition independently comprise a safe and effective amount of cosmetically acceptable carrier. In at least one embodiment, the first—as well as the second—crosslinking composition independently comprises from about 0.1% to about 99%, or from about 1% to about 98%, or from about 10% to about 97%, or from about 30% to about 95% water, by weight of the crosslinking composition.

Other ingredients may be present in the first—as well as the second—crosslinking composition. In at least one embodiment, the first—as well as the second—crosslinking composition comprises antioxidants. Antioxidants are useful in view of providing longer-term stability for the crosslinking composition. In at least one embodiment, the first—as well as the second—crosslinking composition comprises a safe and effective amount of an antioxidant. In at least one embodiment, the first—as well as the second—crosslinking composition comprises from about 0.001% to about 5%, or from about 0.5% to about 1.0% antioxidant. In at least one embodiment, the antioxidant is selected from the group consisting of: ascorbic acid (vitamin C), ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, peroxides including hydrogen peroxide, perborate, thioglycolates, persulfate salts, 6-hydroxy-2,5,7,8-tetramethylchroman-2-carboxylic acid (commercially available under the tradename Trolox™), gallic acid and its alkyl esters, especially propyl gallate, uric acid and its salts and alkyl esters, ferulic acid and its salts and esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, 1-methionine, proline, superoxide dismutase, silymarin, tea extracts, grape skin and/or grape seed extracts, melanin, rosemary extracts, and mixtures thereof. In at least one embodiment, the antioxidant is tocopherol sorbate or an ester of tocopherol. In at least one embodiment, the antioxidant is sodium benzoate. In at least one embodiment, the antioxidant is ferulic acid. Ferulic acid has the benefit of enhancing the oxidative stability of the formulation. In at least one embodiment, the acidic first—as well as the second—crosslinking composition comprises a safe and effective amount of ferulic acid. In at least one embodiment, the crosslinking composition comprises from about 0.001% to about 5%, or from about 0.5% to about 1.0% ferulic acid.

In at least one embodiment, the first—as well as the second—crosslinking composition comprises a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage, in order to decrease the local iron load, which generates, as indicated above, a pro-oxidant situation and pigmentation. A chelating agent is useful in view of providing longer-term stability for the crosslinking composition. In at least one embodiment, the first—as well as the second—crosslinking composition comprises a safe and effective amount of a chelator or chelating agent. In at least one embodiment, the first—as well as the second—crosslinking composition comprises a chelating agent, and wherein the chelating agent is selected from the group consisting of: N-hydroxysuccinimide, EDTA, NTA, deferoxamine, hydroxamic acids and their salts, phytic acid, phytate, gluconic acid and its salts, transferrine, lactoferrin, and mixtures thereof. In at least one embodiment, the first—as well as the second—crosslinking composition comprises a safe and effective amount of chelating agent. In at least one embodiment, the first—as well as the second—crosslinking composition comprises from about 0.001% to about 10%, or from about 0.01% to about 5%, or from about 0.1% to about 5%, or from about 0.5% to about 1.0% chelating agent. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. In at least one embodiment, the chelating agent is selected from the group consisting of: N-hydroxysuccinimide deferoxamine, lactoferrin, hydroxamic acids, gluconic acid, phytic acid, derivatives thereof, and mixtures thereof.

In at least one embodiment, the first—as well as the second—crosslinking composition is in a form suitable for application onto hair. In at least one embodiment, the first as well as the second—crosslinking composition is in the form of an emulsion, a solution, or a dispersion. In at least one embodiment, the crosslinking composition comprises a surfactant. The surfactant can be useful in providing an emulsion. In at least one embodiment, when being in the form of an emulsion, said emulsion may be a water-in-oil emulsion, an oil-in-water emulsion, or a multiple emulsion. An emulsion has the benefit of providing an easy-to-apply composition for the consumer to apply to the hair and has aesthetic advantages. The first—as well as the second crosslinking composition may be a leave-in composition or a rinse-off composition. The first—as well as the second—crosslinking composition may be the form of a hair conditioning composition. The first—as well as the second—crosslinking composition may further comprise at least one cosmetic agent selected from hairstyling polymers, conditioning agents, hair cleansing agents, or mixtures thereof. In at least one embodiment, the first—as well as the second crosslinking composition comprises a hairstyling polymer. In at least one embodiment, the hairstyling polymer is selected from the group consisting of: non-ionic hairstyling polymer, anionic hairstyling polymer, zwitterionic and/or amphoretic hairstyling polymer, cationic hair styling polymer, or mixtures thereof. Suitable hairstyling polymers may be found in the CTFA International Cosmetics Ingredient Dictionary and Handbook, "Hair Fixatives", 12$^{th}$ edition (2008). Suitable hairstyling polymers are, for example, those materials disclosed from page 12, line 5 to page 19, line 1 of the European patent application 08151246.9 filed on 11 Feb. 2008, which is incorporated herein by reference.

In at least one embodiment, the first—as well as the second—crosslinking composition comprises from about 0.01% to about 10% by weight, or from about 0.1% to about 8%, or from about 0.1% to about 5% hairstyling polymer.

In at least one embodiment, the crosslinking compositions comprise a non-ionic hairstyling polymer. In at least one embodiment, the non-ionic hairstyling polymer is a natural or synthetic polymer. In at least one embodiment, the non-ionic hair styling polymers is a polymer obtained from the polymerization of at least one type of monomer selected from: vinylpyrrolidone; vinylcaprolactam; vinyl esters; vinyl alcohol; vinyl acetate; (meth)acrylamide, and/or its derivatives; (meth)acrylic acid, its salts, and/or its derivatives; propylene and/or ethylene glycol acid; crotonic acid; or mixtures thereof. For example, such polymers are available under the trade names Luviskol® or Luviset Clear®.

In at least one embodiment, the crosslinking compositions comprise an anionic hairstyling polymer. In at least one embodiment, the anionic hairstyling polymer is selected from the group consisting of: acrylic acid/alkyl acrylate/ Nalkylacrylamide terpolymer; vinyl acetate/crotonic acid copolymer; C1-C5-alkyl acrylate/(meth)acrylic acid copolymer; sodium polystyrenesulfonate; vinyl acetate/crotonic acid/vinyl alkanoate copolymer; vinyl acetate/crotonic acid/vinyl neodecanoate copolymer; aminomethylpropanol acrylate copolymer; vinylpyrrolidone/(meth)acrylic copolymer; methyl vinyl ether/maleic monoalkyl esters copolymer; aminomethylpropanol salts of allyl methacrylate/(meth)acrylate copolymer; ethyl acrylate/methacrylic acid copolymer; vinyl acetate/mono-nbutyl maleate/isobornyl acrylate copolymer; octylacrylamid/(meth)acrylic acid copolymer; polyesters of diglycol, cyclohexanedimethanol, isophthalic acid and sulfoisophthalic acid; and mixtures thereof.

In at least one embodiment, the first—as well as the second—crosslinking composition comprises a zwitterionic or amphoteric hairstyling polymer. In at least one embodiment, the zwitterionic or amphoteric hairstyling polymer is selected from the group consisting of: alkylacrylamide/alkylaminoalkyl methacrylate/(meth)acrylic acid copolymers; copolymers which are formed from at least one first monomer type which has quaternary amine groups, and at least one second monomer type which has acid groups; copolymers of fatty alcohol acrylates, of alkylamine oxide methacrylate and at least one monomer chosen from acrylic acid and methacrylic acid; methacryloylethylbetaine/methacrylic acid and/or esters copolymers; polyquaternium-47; polyquaternium-43; oligomers or polymers, preparable from quaternary croton betaines or quaternary croton betaine esters; or mixtures thereof.

In at least one embodiment, the first—as well as the second—crosslinking composition comprises a cationic hairstyling polymer. In at least one embodiment, the cationic hairstyling polymer is selected from the group consisting of homopolymers or copolymers where a quaternary nitrogen groups are present either in the polymer chain or as substituent on one or more of the cationic monomers. The monomers containing ammonium groups may be copolymerized with non-cationic monomers. Suitable cationic monomers may be unsaturated, free-radically polymerizable compounds which carry at least one cationic group, in particular ammonium-substituted vinyl monomers, such as, for example, trialkylmethacryloxyalkylammonium, trialkylacryloxyalkylammonium, dialkyldiallylammonium and quaternary vinylammonium monomers with cyclic, cationic nitrogen-containing groups, such as pyridinium, imidazolium or quaternary pyrrolidones, e.g. alkylvinylimidazolium, alkylvinylpyridinium, or alkylvinylpyrrolidone salts. The alkyl groups of these monomers are preferably lower alkyl groups, such as, for example, C1 to C7-alkyl groups, particularly preferably C1 to C3-alkyl groups. Suitable non-cationic monomers may be selected from (meth)acrylamide, derivatives thereof; acrylate, its derivative thereof; vinylcaprolactone, vinylcaprolactam, vinylpyrrolidone, vinyl esters, vinyl alcohol, propylene glycol or ethylene glycol. For example, suitable cationic hairstyling polymers are available under the tradenames Gafquat 755 N; Gafquat 734; Gafquat HS 100; Luviquat HM 550; Merquat Plus 3300; Gaffix VC 713; Aquaflex SF 40. In at least one embodiment, the crosslinking compositions comprise a cationic hairstyling polymer derived from a natural polymer. In at least one embodiment, the cationic hairstyling polymer derived from a natural polymer is derived from a natural polymer selected from the group consisting of: cationic derivatives polysaccharides such as cellulose, starch and/or guar; chitosan, its salts, and/or its derivatives; or mixtures thereof. In at least one embodiment, the cationic hairstyling polymers are selected from the group consisting of: polyquaternium-4; polyquaternium-10; polyquaternium-24; guar hydroxypropyltrimonium chloride; chitosonium pyrrolidonecarboxylate; and mixtures thereof.

In at least one embodiment, the first—as well as the second—crosslinking composition comprises a conditioning agent, or a hair conditioning agent. The first—as well as the second—crosslinking composition may comprise any suitable and conventional hair conditioning agents. The term "hair conditioning agent" herein means any cosmetically acceptable compound having a cosmetic effect on hair, such as providing gloss to hair, making hair more manageable, improving hair touch, improving combability and/or giving hair more volume. Suitable hair conditioning agents may be found in the CTFA International Cosmetics Ingredient Dictionary and Handbook, "Hair conditioning agents", $12^1$ edition (2008). In at least one embodiment, the hair conditioning agent is selected from the group consisting of: cationic surfactants, non-ionic surfactants, silicone compounds, organic oily conditioning agents, and mixtures thereof. Suitable hair conditioning agents are, for example, those materials disclosed from page 19, line 3 to page 27, line 33 of the European patent application 08151246.9 filed on 11 Feb. 2008, which is incorporated herein by reference.

In at least one embodiment, the conditioning agent is a cationic surfactant. In at least one embodiment, the cationic surfactant comprises amino or quaternary ammonium moieties. In at least one embodiment, the first—as well as the second—crosslinking composition comprises from about 0.05% to about 3.5%, or from about 0.1% to about 3.0%, or from about 0.5% to about 2.5%, or from about 1.0% to about 2.0% cationic surfactant. In at least one embodiment, the cationic surfactant is according to Formula II:

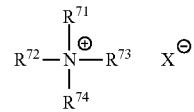

wherein at least one of $R^{71}$, $R^{72}$, $R^{73}$ and $R^{74}$ is selected from: an aliphatic group of from 8 to 30 carbon atoms; an aromatic, alkoxy, polyoxyalkylene, alkylamido, hydroxyalkyl, aryl; or an alkylaryl group having from 7 to 22 carbon atoms; wherein the remainder of $R^{71}$, $R^{72}$, $R^{73}$ and $R^{74}$ are independently selected from the group consisting of: an aliphatic group consisting of from 1 to 22 carbon atoms; and an aromatic, alkoxy, polyoxyalkylene, alkylamido, hydroxyalkyl, aryl or alkylaryl group having up to 22 carbon atoms; wherein X is selected from the group consisting of: halogen, acetate, citrate, lactate, glycolate, phosphate, nitrate, sulfonate, sulfate, alkylsulfate, alkyl sulfonate radicals, and mixtures thereof. In at least one embodiment, cationic surfactant is according to Formula II (see above), wherein at least one of $R^{71}$, $R^{72}$, $R^{73}$ and $R^{74}$ is an aliphatic group having from 16 to 24 carbon atoms; wherein the remainder of $R^{71}$, $R^{72}$, $R^{73}$ and $R^{74}$ are independently selected from the group consisting of aliphatic groups having from 1 to 4 carbon atoms; wherein X is selected from the group consisting of: chloride or sulfate. In at least one embodiment, the cationic surfactant is selected from the group consisting of: behenyltrimethylammonium chloride, methyl sulfate or ethyl sulfate; stearyltrimethylammonium chloride, methyl sulfate or ethyl sulfate; and mixtures thereof. It is believed that a longer alkyl group provides improved smoothness and soft feeling on wet and dry hair, compared to cationic surfactants with a shorter alkyl group. It is also believed that such cationic surfactants can provide reduced scalp irritation, compared to those having a shorter alkyl group. In at least one embodiment, the cationic surfactant is a di-long alkyl quaternized ammonium salt selected from the group consisting of: dialkyl (14-18 carbons) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and mixtures thereof. In at least one embodiment, the cationic surfactant is a tertiary amidoamine having an alkyl group of from about 12 to about 22 carbons. In at least one embodiment, the cationic surfactant is selected from the group consisting of: cetyl trimethyl ammonium salts; behenyl trimethyl ammonium salts; dimethyl ditallow ammonium salts; stearyl amidopropyl dimethylamine; (di)esterquats; quaternium 8, 14, 15, 18, 22, 24, 26, 27, 30, 33, 37, 53, 60, 61, 72, 78, 80, 81, 82, 83, 84, and/or 91; or mixtures thereof.

In at least one embodiment, the conditioning agent is a non-ionic surfactant. Suitable non-ionic surfactants may be surfactants having a HLB of less than 8. Suitable nonionic surfactants may be selected from glyceryl esters; sugar esters; alkylpolyglucoside ethers; oleyl- or isostearylpolyglucoside; polyoxyethylene (20) sorbitan monostearate; or mixtures thereof.

In at least one embodiment, the conditioning agent is a silicone compound. In at least one embodiment, the silicone compound is volatile or nonvolatile, and/or soluble or insoluble silicones. For example, suitable silicone conditioning agents are available under the tradenames SF 1075 methyl phenyl fluid (Electric company); DC200 Fluid, DC244, DC245, DC345, Dow 5-7113, DC556 Cosmetic Grade Fluid, DC1248 (Dow Corning). In at least one embodiment, the first—as well as the second—crosslinking composition comprises a conditioning agent being the reaction product of: (a) an aminosilane; (b); polysiloxane; and optionally (c) a polyether. In at least one embodiment, the first—as well as the second—crosslinking composition comprises a conditioning agent being the reaction product of: (a) an aminosilane; (b); polysiloxane; and (c) a polyether. In at least one embodiment, the first—as well as the second crosslinking composition comprises a conditioning agent, and wherein the conditioning agent is selected from the group consisting of: epoxyaminosilane copolymers, and polysiloxane/polyurea block copolymers, and mixtures thereof. In at least one embodiment, the first—as well as the second—crosslinking composition comprises a conditioning agent being the reaction product of: (a) an aminosilane; (b) polysiloxane; and (c) a polyether; and optionally (d) an amine. In at least one embodiment, the polysiloxane is an epoxy encapped polysiloxane. In at least one embodiment, the polysiloxane comprises at least two oxirane or oxetane groups. In at least one embodiment, the polysiloxane comprises from about 10 to about 450 silicon atoms, or from about 40 to about 400 silicon atoms, from about 75 to about 350 silicon atoms, from about 150 to about 250 silicon atoms. In at least one embodiment, the polysiloxane is an epoxy encapped polysiloxane. In at least one embodiment, the polyether has the structure $CH_2(O)CHCH_2O(CH_2(CH_3)CH_2O)$—$CH_2CH(O)CH_2$ (average) wherein n is an integer from 1 to 10. In at least one embodiment, the amine comprises from 1 to 10 carbon atoms, or from 2 to 5 carbon atoms. In at least one embodiment, the amine is an alkylamine that is substituted with at least one alkyl group. In at least one embodiment, the amine is selected from the group consisting of: methylamine, ethylamine, propylamine, ethanol amine, isopropylamine, butylamine, isobutylamine, hexylamine, dodecylamine, oleylamine, aniline aminopropyltrimethylsilane, aminopropyltriethylsilane, aminomorpholine, aminopropyldiethylaminebenzylamine, napthylamine 3-amino-9-ethyl carb azole, 1-aminoheptaphlorohexane, 2,2,3,3,4,4,5,5,6,6,7,7,8,8,8-pentadecafluoro-1-octanamine, and mixtures thereof. In at least one embodiment, the amine is selected from the group consisting of: methylethylamine, methylhexylamine, methyloctadecylamine, diethanolamine, dibenzylamine, dihexylamine dicyclohexylamine, piperidine, pyrrolidine phthalimide, and mixtures thereof. In at least one embodiment, the conditioning agent is an epoxyaminosilane copolymer. In at least one embodiment, the conditioning agent is conditioning agent being the reaction product of: (a) an aminosilane; (b) polysiloxane, wherein the polysiloxane comprises from about 10 to about 450 silicon atoms, or from about 40 to about 400 silicon atoms; and (c) a polyether; and (d) an amine, wherein the amine is an alkylamine that is substituted with at least one alkyl group.

In at least one embodiment, the first—as well as the second—conditioning agent is selected from the group consisting of: epoxyaminosilane copolymers, and polysiloxane/polyurea block copolymers, and mixtures thereof. In at least one embodiment, the conditioning agent is a polydimethylsiloxane-derivative comprising aminoalkyl groups and having an amine number of at least 0.1 meq/g of polydimethylsiloxane. Such polydimethylsiloxane-derivative can, for example, be methoxy-terminated or hydroxy-terminated, or mixtures thereof.

In at least one embodiment, the conditioning agent is an organic oily conditioning agent. In at least one embodiment, the organic oily conditioning agent is non-volatile, water-insoluble, oily or fatty. Organic oily conditioning agents may be selected from hydrocarbon oils and fatty esters. In at least one embodiment, the conditioning agent is a fatty alcohol. In at least one embodiment, the fatty alcohol is a non-volatile low melting point fatty alcohol. In at least one embodiment, the conditioning agent is a fatty alcohol and the fatty alcohol is selected from the group consisting of: capryl alcohol, lauryl alcohol, stearyl alcohol, cetyl alcohol, myristyl alcohol, palmitoleyl alcohol, and mixtures thereof.

The first—as well as the second—crosslinking composition may further comprise at least one direct hair dye. In at least one embodiment, the crosslinking compositions comprises from about 0.01% to about 15%, or from about 0.1% to about 10%, or from about 0.5% to about 8% direct hair dye.

The first—as well as the second—crosslinking composition may further comprise at least one viscosity-modifying agent. In at least one embodiment, the crosslinking compositions comprise from about 0.01% to about 20%, or from about 0.05% to about 10%, or from about 0.1% to about 5% viscosity-modifying agent.

The first—as well as the second—crosslinking composition may further comprise at least one emulsifier and/or surfactant. In at least one embodiment, the emulsifier and/or surfactant is selected from nonionic surfactants; anionic surfactants; amphoretic surfactants; or mixtures thereof. In at least one embodiment, the first—as well as the second—crosslinking composition comprises from about 0.01% to about 20%, or from about 0.05% to about 10%, or from about 0.1% to about 5%, emulsifier and/or surfactant.

The acidic as well as the caustic crosslinking composition may further comprise at least one pigment. In at least one embodiment, the pigment is selected from natural pigments; synthetic pigments; or mixtures thereof. The pigments may be selected from organic pigment, inorganic pigment; or mixtures thereof. The pigments may be selected from colored pigments; pearlescent pigments; or mixtures thereof. Said first—as well as the second—crosslinking composition may comprise from about 0.01% to 10%, or from about 1% to about 2% pigment present in the product mass in undissolved form by weight of the total first—as well as the second crosslinking composition. The first—as well as the second—crosslinking composition may comprise pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water-soluble components such as those having C. I. Names.

In at least one embodiment, the first—as well as the second—crosslinking composition comprises at least one particulate substance. In at least one embodiment, the particulate substance is selected from silica; silicates; aluminates; clay earths; mica; insoluble salts, particularly insoluble inorganic metal salts; metal oxides; minerals; insoluble polymer particles; or mixtures thereof. In at least one embodiment, the first—as well as the second crosslinking composition comprises from about 0.01% to about 10%, or from about 0.05% to about 5% of at least one particulate substance. In at least one embodiment, the first—as well as the second—crosslinking composition is substantially free of a particulate substance such as clay.

In at least one embodiment, the first—as well as the second—crosslinking composition comprises at least one preservative. In at least one embodiment, the first—as well as the second—crosslinking composition may comprise from about 0.01% to about 5% by weight, or from about 0.05% to about 1% preservative.

A variety of additional optional ingredients may be incorporated into the first—as well as the second—crosslinking composition of the present invention. Non-limiting examples of these additional ingredients may be selected from preservatives; antioxidants; sequestering agents; solvents; fragrances & perfumes; fillers; screening agents; odor absorbers; coloring materials; lipid vesicles; detersive surfactants; thickening agents and suspending agents; viscosity modifiers; pearlescent aids; UV-filters and sunscreens; agents for combating free radicals; polyvinyl alcohol; pH adjusting agents; salts; coloring agents; polymer plasticizing agents; direct dyes; or mixtures thereof. The acidic as well as the caustic crosslinking composition may comprise from about 0%, or from about 0.1% to about 5% antimicrobial agents. In at least one embodiment, the acidic as well as the caustic crosslinking composition comprises an organic acid selected from the group consisting of: glycine, L-methionine, L-arginine, biotin, creatine, and mixtures thereof. In at least one embodiment, the first—as well as the second—crosslinking composition comprises panthenol. In at least one embodiment, the first as well as the second—crosslinking composition comprises a wax compound. In at least one embodiment, the first—as well as the second—crosslinking composition comprises beeswax.

In at least one embodiment, the first—as well as the second—crosslinking composition has a viscosity, measured at 25° C., of from about 0.1 mPas to about 1,000,000 mPas, or from about 1 mPas to about 80,000 mPa·s, or from about 5 mPas to about 3,500 mPa·s. The viscosity is measured by HAAKE Rotation Viscometer VT 550 with cooling/heating vessel and sensor systems according to DIN 53019 (MV-DIN, SV-DIN), shear rate is 12.9 $s^{-1}$.

In at least one embodiment, the first—as well as the second—crosslinking composition comprises a buffering agent. In at least one embodiment, the buffering agent is a phosphate buffer. In at least one embodiment, the buffering agent is a borate buffer or a carbonate buffer. In at least one embodiment, the buffering agent is selected from the group consisting of: glycine/sodium hydroxide; sodium carbonate/sodium hydrogen carbonate, sodium tetraborate/sodium hydroxide; sodium bicarbonate/sodium hydroxide; ammonium chloride/ammonia. The buffering agent has the advantage of controlling the pH, which aids the stability of the crosslinking compositions. In at least one embodiment, the first crosslinking composition comprises an acidifying agent. Such acidifying agent can be organic or inrorganic and can be mono-functional or poly-functional. In at least one embodiment, the acidifying agent used to adjust the pH value of the first formula is identical to the at least bi-functional Brønsted-acid of the first formula. In at least one embodiment, the second crosslinking composition comprises an alkalizing agent. Such alkalizing agent can be organic or inrorganic and can be mono-functional or poly-functional. In at least one embodiment, the alkalizing agent used to adjust the pH value of the second formula is identical to the at least bi-functional Brønsted-base of the first formula.

Method

Described herein is a hair strengthening and/or hair repairing method comprising: (a) applying a first—crosslinking composition to hair and leaving the first—hair strengthening composition on for 1 to 45 minutes; (b) optionally rinsing, shampoo'ing and/or drying the hair drying; (c) applying a second—crosslinking composition to hair and leaving the second—hair strengthening composition on for 1 to 45 minutes; (d) optionally rinsing, shampoo'ing and/or drying the hair drying. Prior to step (a) the hair strengthening composition can be mixed with commercially available hair coloring or bleaching formulations. If mixed with commercially available hair coloring or bleaching formulations the method steps are in the order (a) then (b) then (c) then (d)- or -(c) then (d) then (a) the-n (b). In the method of the present invention, the first—as well as the second—crosslinking composition may be applied on wet hair and/or on dry hair.

In an embodiment, prior to the first step of the method which can either be step (a) or step (c) the hair is washed with a shampoo, for example a cleansing shampoo. In an embodiment, at the end of the treatment cycle, thus following either step (b) or step (d), depending on if the method started with step (a) or step (c), the hair is conditioned with a conditioning formulation comprising a conditioning agent. Conditioning agents are disclosed herein and are suitable for this embodiment. In an embodiment, the hair is dried using a blow dryer and a brush.

In an embodiment, the method relates to a hair strengthening and/or hair repairing method comprising: (a) applying a first—hair care composition to hair, wherein the hair care composition comprises an at least bi-functional Brønsted-base of the general formula X—R—Y, wherein X and Y are proton-acceptor groups and R is an organic spacer comprising 1 to 20 carbon atoms, and 0 to 5 oxygen atoms, and 0 to 5 nitrogen atoms, and X—R—Y having a molecular weight of less than 500 g/mol, and leaving the first—hair strengthening composition on for 1 to 45 minutes, (b) optionally rinsing, shampoo'ing and/or drying the hair—, (c) applying to the hair a second—formula comprising a crosslinking composition comprising an at least bi-functional organic acid capable of reacting with the amine groups of the hair, and leaving the second—hair strengthening composition on for 1 to 45 minutes, (d) optionally rinsing, shampoo'ing and/or drying the hair, characterized in that the first formula and the second formula both have a pH of 1.5 to 7.

Optionally, the hair strengthening composition of step (a) or (c) can be mixed into commercially available hair coloring or hair bleaching formulations prior to the application. The hair strengthening method can be altered such that the hair strengthening composition of step (c) is applied before hair strengthening composition of step (a) is.

Applying a Hair Care Composition to Hair

The present invention relates to a hair strengthening and/or repairing method comprising: (a) applying a first—hair care composition to hair, wherein the first hair care composition comprises an at least bi-functional Brønsted-base of the general formula X—R—Y, wherein X and Y are proton-acceptor groups and R is an organic spacer comprising 1 to 20 carbon atoms, and 0 to 5 oxygen atoms, and 0 to 5 nitrogen atoms, and X—R—Y having a molecular weight of less than 500 g/mo, and (c) applying to the hair a second—hair strengthening composition comprising a crosslinking composition comprising an at least bi-functional organic acid capable of reacting with the amine groups of the hair, involving applying onto hair from about 0.01 gram to about 5 gram of said compositions per gram hair. In an embodiment, —the first and the second composition—are on the hair for at least 1 min, or from about 5 min to about 45 min, or from about 10 min to about 40 min, or from about 20 min to about 35 min, prior to carrying out the remaining step, either (a) or (c), depending on if the method was started with step (a) or (c).

Hair Drying

The hair—strengthening method may optionally comprise hair drying in steps (b) and/or (d). In an embodiment, the hair drying is carried out by a blow drier. In an embodiment, the hair drying is carried out for a duration of from about 1 min to about 45 min, or from about 2 min to 20 min, or from about 5 min to 15 min. In general, following the hair drying, the hair can still be damp, but needs to have reasonable e.g. 75% hair fibre separation of the head of hair. Some residual moisture in the hair is acceptable. In an embodiment, the hair drying is carried out by a hood appliance. In an embodiment, the hair drying is carried out by toweling hair and/or by pressing hair with hands.

Hair dryer or blow dryer distances between device and head are typically down to about 10 cm. Blow dryers direct hot air through some sort of attachment for combing or otherwise treating the hair. A blow dryer is typically used such that the distance to the hair (for example at a distance of 20 or 30 or 40 centimeters) and often is used with the aid of a comb or a brush. In an embodiment, the hair drying is carried out by a blow drier at a temperature of from about from 50° C. to about 100° C. In an embodiment, the hair drying is carried out by a blow drier at a temperature of up to 130° C. In an embodiment, the hair drying is carried out with a blow drier with brushing to help styling the hair.

In an embodiment, the hair strengthening and/or repairing method comprises in addition to steps (a), (b), (c), (d) also a hair straightening step (e). The hair straightening step (e) comprises using a hair straightening appliance comprises metal or ceramic plates. In an embodiment, the metal or ceramic plates are provided to a temperature of from about 100° C. to about 280° C. In an embodiment, the metal or ceramic plates are provided to a temperature of from about 110° C. to about 250° C., or from about 120° C. to about 240° C., or from about 140° C. to about 230° C., or from about 160° C. to about 220° C., or from about 180° C. to about 210° C., or from about 190° C. to about 200° C.

In an embodiment, method (a) to (d) is repeated from 2 to 4 times per month on an ongoing basis for the purpose of strengthening hair and reducing hair damage.

In an embodiment, the first—crosslinking composition may comprise a first, second, and third crosslinking agent. The first crosslinking agent may be 4,7,10-Trioxa-1,13-tridecanediamine, the second may be 4,9-Dioxa-1,12-dodecanediamine, and the third crosslinking agent may be 1,11-Diamino-3,6,9-trioxaundecane.

In an embodiment, the crosslinking composition may comprise:
  from about 0.01-% to about 30-% 4,7,10-Trioxa-1,13-tridecanediamine, 4,9-Dioxa-1,12-dodecanediamine, and 1,11-Diamino-3,6,9-trioxaundecane, present at a weight ratio of 1:1:1, 2:1:1, or 4:1:1
  optionally, a buffering agent;
  optionally a pH adjusting agent;
  a cosmetically acceptable carrier;
  a conditioning agent being the reaction product of: (a) an aminosilane; (b); polysiloxane; and optionally (c) a polyether;
and wherein the composition has a pH of from about pH 7 to about pH 12.

In an embodiment, the formulation comprises from about 0.01% to about 15%, or from about 0.1% to about 10%, or from about 1-% to about 5% conditioning agent being the reaction product of: (a) an aminosilane; (b); polysiloxane; and optionally (c) a polyether. In an embodiment, the conditioning agent is the reaction product of: (a) an aminosilane; (b); polysiloxane; (c) a polyether.

In an embodiment, a kit may comprise: (i) a first—crosslinking composition; (ii)—a second crosslinking composition; (iii) a conditioning composition. In an embodiment, the kit may be for strengthening and repairing damaged hair. In an embodiment, the kit may be for improving ease of hair styling.

In an embodiment, the crosslinking agent may be used for strengthening hair and/or repairing damaged hair. In an embodiment, the first—as well as the second—crosslinking composition may be used for improving ease of styling of the hair.

EXAMPLES

The following examples further describe and demonstrate embodiments within the scope of the present invention. The examples are given solely for the purpose of illustration, and are not to be construed as limitations of the present invention since many variations thereof are possible without departing from its scope.

Example Compositions for the First—Crosslinking Composition (Total Mass 100 g):

Liquid A:
10 g 4,7,10-Trioxa-1,13-tridecanediamine, 5 g 4,9-Dioxa-1,12-dodecanediamine, 5 g 1,11-Diamino-3,6,9-trioxaundecane, 2 g epoxyaminosilane copolymer, 20 g Citric Acid, QSP water Liquid B:
25 g 4,7,10-Trioxa-1,13-tridecanediamine, 9 g Phosphoric Acid, QSP water Liquid C:
12 g 4,7,10-Trioxa-1,13-tridecanediamine, 3 g 4,9-Dioxa-1,12-dodecanediamine, 3 g 1,11-Diamino-3,6,9-trioxaundecane, 2 g epoxyaminosilane copolymer, 13 g Malic Acid, QSP water Rinse-Out Conditioner A:
16 g 4,7,10-Trioxa-1,13-tridecanediamine, 8 g 4,9-Dioxa-1,12-dodecanediamine, 16 g Citric Acid, 1.00 g cetyltrimethyl ammonium chloride, 1.00 g polymethylphenyl siloxane, 0.40 g phenoxy ethanol, 0.20 g PHB-methylester, 1.00 g Dow Corning 949 Cationic Emulsion®, 5.00 g isododecane, 0.40 g perfume oil, QSP water.

Rinse-Out Conditioner B:
18 g 4,7,10-Trioxa-1,13-tridecanediamine, 7 g Phosphoric Acid, 1.00 g cetyltrimethyl ammonium chloride, 1.00 g polymethylphenyl siloxane, 0.40 g phenoxyethanol, 0.20 g PHB-methylester, 8.00 g Dow Corning 57113 Cationic Emulsion®, 5.00 g isododecane, 0.40 g perfume oil, QSP water.

Leave-in Conditioner A:
6 g 4,7,10-Trioxa-1,13-tridecanediamine, 3 g 4,9-Dioxa-1,12-dodecanediamine, 6.5 g Malic Acid, 1.00 g cetyltrimethyl ammonium chloride, 1.00 g polymethylphenyl siloxane, 0.40 g phenoxy ethanol, 0.20 g PHB-methylester, 8.00 g Momentive™ Cationic Emulsion®, 5.00 g isododecane, 0.40 g perfume oil, QSP water.

Leave-in Conditioner B:
10 g 4,7,10-Trioxa-1,13-tridecanediamine, 5 g 1,11-Diamino-3,6,9-trioxaundecane, 15 g Citric Acid, 0.10 g vitamin E-acetate, 0.50 g polymethylphenyl siloxane, 10.00 g propylene glycol, 0.50 g behenyl trimethylammonium chloride, 0.05 g sodium chloride, 0.30 g d-panthenol, 0.30 g PHB-propylester, 2.00 g isododecane, 0.20 g perfume oil, QSP water.

Example Compositions for the Second—Crosslinking Composition (Total Mass 100 g):

Liquid A':
15 g Mal-ic Acid, 18 g Monoethanolamine QSP water

Liquid B':
25 g Itaconic Acid, 6 g Ammonia QSP water

Liquid C':
12 g Maleic Acid, 12 g Itaconic Acid, 3 g 1,11-Diamino-3,6,9-trioxaundecane, 2 g epoxyaminosilane copolymer, QSP water Rinse-Out Conditioner A':
12 g Maleic Acid, 12 g Monoethanolamine 1.00 g cetyltrimethyl ammonium chloride, 1.00 g polymethylphenyl siloxane, 0.40 g phenoxy ethanol, 0.20 g PHB-methylester, 1.00 g Dow Corning 949 Cationic Emulsion®, 5.00 g isododecane, 0.40 g perfume oil, QSP water.

Rinse-Out Conditioner B':
6 g Maleic Acid, 6 g Itaconic Acid, 10 g Monoethanolamine 1.00 g cetyltrimethyl ammonium chloride, 1.00 g polymethylphenyl siloxane, 0.40 g phenoxyethanol, 0.20 g PHB-methylester, 8.00 g Dow Corning 57113 Cationic Emulsion®, 5.00 g isododecane, 0.40 g perfume oil, QSP water.

Leave-in Conditioner A':
6 g Mal-ic Acid, 4 g 4,7,10-Trioxa-1,13-tridecanediamine, 1.00 g cetyltrimethyl ammonium chloride, 1.00 g polymethylphenyl siloxane, 0.40 g phenoxy ethanol, 0.20 g PHB-methylester, 8.00 g Momentive™ Cationic Emulsion®, 5.00 g isododecane, 0.40 g perfume oil, QSP water.

Leave-in Conditioner B':
3 g Maleic Acid, 3 g Itaconic Acid, 0.10 g vitamin E-acetate, 0.50 g polymethylphenyl siloxane, 10.00 g propylene glycol, 0.50 g behenyl trimethylammonium chloride, 0.05 g sodium chloride, 0.30 g d-panthenol, 0.30 g PHB-propylester, 2.00 g isododecane, 0.20 g perfume oil, QSP water.

Data

The hair strengthening efficacy is tested for the first—as well as the second crosslinking compositions of the present invention. Switches of low lift natural hair are employed. These are shampooed with a K-PAK clarifying shampoo to ensure the hair is in a clean state with no residues that could affect the end result. The switches are then rinsed. Excess water is removed from the hair by wringing out the switches. The switches are treated with a crosslinking composition which comprises active agents as listed in TABLE 1 and QSP water buffered—at pH 4—. These ingredients are mixed on a spinner plate for 15 mins. 0.5 g of crosslinking composition per 1 g hair is employed. The crosslinking composition is left on the hair for 30 minutes. After this time, the hair is blow dried and brushed with a standard metal comb for 500 strokes. Hair strengthening and hair damage is assed via recording of the weight of broken hair fibers collected from the combing and normalized to the weight of the hair switches. 5 hair switches per experiment are treated and combed, results are averaged. When a first and a second treatment were employed, hair switches were—treated—without an inbetween—hair drying step-.

TABLE 1

| Hair breakage results after n combing strokes | | | |
|---|---|---|---|
| Treatment | 50 strokes | 250 strokes | 500 strokes |
| Reference: Untreated hair | 5.0% | 8.1% | 9.7% |
| 25% Maleic Acid (pH adjusted to pH 5 with Monoethanlamine) | 3.2% | 4.3% | 6.1% |
| 25% Itaconic Acid (pH adjusted to pH 5 with Monoethanlamine) | 2.9% | 4.1% | 6.2% |
| 12% Maleic Acid + 12% Itaconic Acid (pH adjusted to pH 5 with Monoethanlamine) | 2.9% | 4.4% | 5.9% |
| 15% 4,7,10-Trioxa-1,13-tridecanediamine (pH adjusted to pH 5 with Phosphoric Acid) | 2.9% | 4.1% | 6.3% |
| 15% 4,9-Dioxa-1,12-dodecanediamine (pH adjusted to pH 5 with Phosphoric Acid) | 3.1% | 3.9% | 5.9% |
| 15% 1,11-Diamino-3,6,9-trioxaundecane (pH adjusted to pH 5 with Phosphoric Acid) | 3.1% | 4.2% | 6.2% |
| First: 25% Maleic Acid (pH adjusted to pH 5 with Monoethanlamine) Second: 15% 4,7,10-Trioxa-1,13-tridecanediamine (pH adjusted to pH 5 with Phosphoric Acid) | 1.0% | 2.3% | 3.2% |
| First: 25% Maleic Acid (pH adjusted to pH 5 with Monoethanlamine) Second: 15% 4,9-Dioxa-1,12-dodecanediamine (pH adjusted to pH 5 with Phosphoric Acid) | 1.1% | 2.1% | 3.2% |

TABLE 1-continued

Hair breakage results after n combing strokes

| Treatment | 50 strokes | 250 strokes | 500 strokes |
| --- | --- | --- | --- |
| First: 25% Maleic Acid (pH adjusted to pH 5 with Monoethanlamine)<br>Second: 1,11-Diamino-3,6,9-trioxaundecane (pH adjusted to pH 5 with Phosphoric Acid) | 1.0% | 1.9% | 3.4% |
| First: 25% Itaconic Acid (pH adjusted to pH 5 with Monoethanlamine)<br>Second: 5% 4,7,10-Trioxa-1,13-tridecanediamine + 5% 4,9-Dioxa-1,12-dodecanediamine + 5% 1,11-Diamino-3,6,9-trioxaundecane (pH adjusted to pH 5 with Phosphoric Acid) | 1.2% | 2.3% | 3.3% |

When averaging over five experimental results, the relative standard deviation is less than 15%. As can be seen in Table 1, the sequential application of a first—hair strengthening composition of the present invention with second—hair strengthening composition of the present invention significantly reduces hair breakage. The hair feel properties after the treatment of the hair with the and first and the second composition of the present invention are excellent and the treated hair posses great shine. Same hair breakage reduction results and hair feel property improvements were achieved when the first—hair strengthening composition was first mixed into a commercially available hair coloring formulation, left on the hair switch for a time specified by the hair color manufacturer's guidance, followed by applying the second—hair strengthening composition as per instructions above, followed by subsequent hair drying.

To color human hair using oxidative dye technology it is generally necessary to treat the hair with a mixture of suitable oxidative coloring agents and at least one dye oxidizing agent. Hydrogen peroxide is the most commonly used dye oxidizing agent. However, in addition to dye oxidation, hydrogen peroxide treatment of the hair can also solubilize the colored melanin component in the hair and can lead to undesirable hair qualities, such as poor condition, due to increased brittleness and hair damage. These undesirable qualities are in part due to the necessary conditions of conventional peroxide treatment, as part of the hair coloring process, which requires high pH (>pH 9), extended exposure (from 10 to 60 minutes) and relatively high concentration of oxidizing solutions (up to 20% volume of oxygen) in order to deliver effective dye oxidization. Thus there is a need for hair coloring compositions which can oxidize dyes and color the hair effectively and, at the same time, strengthen the hair to provided prevent hair damage.

The process for hair bleaching is very similar to the process of hair coloring. Bleaching, basically, is a process of removing the natural color from hair. Because of the virtually unlimited variations of hair colors, bleaching per so, does not usually produce a uniform or aesthetically pleasing color in hair, nor will it produce a color tone other than that inherent in the hair. For these reasons hair that has been bleached is subsequently treated with a hair toner, a composition containing a hair dye which imparts the desired end-color to the bleached hair. The degree to which the natural color must be bleached from the hair is primarily determined by the desired end color. The toners do not lighten the shade of hair to any great extent; they impart their tone coloration to hair pre-bleached to the basic blonde shade desired, e.g. pastel blonde color tone is achieved in hair pro-bleached to pale blonde not in hair pre-bleached only to a light brown.

Applied by itself or—mixed with commercially available hair coloring or hair bleaching formulations, followed by subsequent application of the second—hair strengthening composition, treating hair with the first—as well as the second—hair strengthening composition of the present invention improves the quality of the hair, reduces hair breakage, reduces hair damage, improves hair feel, reduces hair roughness, improves luster and hair shine, eases hair styling and improves moisture resistance of the hair.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "10%" is intended to mean "about 10%".

Every document cited herein, including any cross referenced or related patent or patent publication, is hereby incorporated herein by reference in its entirety unless expressly excluded or otherwise limited. The citation of any document is not an admission that it is prior art with respect to any document disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for treating hair comprising the steps of:
   (a) applying to the hair a composition (a) comprising an at least bi-functional Brønsted-base of the general composition X—R—Y, wherein X and Y are proton-acceptor groups and wherein R is an organic spacer comprising 1 to 20 carbon atoms, and 0 to 5 oxygen atoms, and 0 to 5 nitrogen atoms and no aromatic or heteroaromatic carbon, and wherein X—R—Y has a molecular weight of less than 500 g/mol, and
   (b) applying to the hair a composition (b) comprising an at least bi-functional organic acid capable of reacting with the amine groups of the hair,
   wherein composition (a) and composition (b) both have a pH of less than 7.

2. The method of claim 1, wherein the hair is dried between steps (a) and (b) and the drying time is 1 to 60 minutes.

3. The method of claim 1, wherein the composition of step (a) or of step (b) is left on the hair for 1 to 45 minutes.

4. The method of claim 1, wherein step (a) is performed prior to step (b).

5. The method of claim 1, wherein step (b) is performed prior to step (a).

6. The method of claim 1, wherein the proton-acceptor groups X and Y of the at least bi-functional Brønsted-base of composition (a) are independently selected from the group consisting of carboxylate, nitrate, hydrogen phosphate, phosphate, primary amine, secondary amine, sulphate, and carbonate.

7. The method of claim 1, wherein there is a waiting time in between steps (a) and (b) or (b) and (a) of 1 to 60 minutes.

8. The method of claim 1, wherein the composition of step (a) is mixed into a commercially available hair coloring or hair bleaching formulation prior to the application to the hair.

9. The method of claim 1, wherein prior to the application of step (a) the hair is treated with a thioglycolic acid-containing hair care composition.

10. The method of claim 1, wherein the at least bi-functional Brønsted-base of the general composition X—R—Y of composition (a) comprises 4,7,10-trioxa-1,13-tridecanediamine, 4,9-dioxa-1,12-dodecanediamine, 1,11-diamino-3,6,9-trioxaundecane, or a mixture thereof.

11. The method of claim 1, wherein the at least bi-functional organic acid of composition (b) comprises maleic acid, itaconic acid, or a mixture thereof.

12. A kit for treating hair according to the method of claim 1, the kit comprising two separate compositions (a) and (b), wherein composition (a) comprises an at least bi-functional Brønsted-base of the general composition X—R—Y, wherein X and Y are proton-acceptor groups, and wherein R is an organic spacer comprising 1 to 20 carbon atoms, and 0 to 5 oxygen atoms, and 0 to 5 nitrogen atoms and no aromatic or heteroaromatic carbon, and wherein X—R—Y has a molecular weight of less than 500 g/mol, and wherein composition (b) comprises an at least bi-functional organic acid capable of reacting with the amine groups of the hair, and composition (a) and composition (b) both have a pH of less than 7.

13. The kit of claim 12, wherein the concentration of the at least bifunctional X—R—Y in composition (a) is 0.01-30%.

14. The kit of claim 12, wherein the concentration of the at least bi-functional organic acid in composition (b) is 0.01-30%.

15. The kit of claim 12, wherein composition (a) further comprises an acidifying agent selected from the group consisting of an inorganic acid, a mono-functional organic acid or a poly-functional organic acid, and wherein composition (b) further comprises an alkalizing agent.

16. The kit of claim 15, wherein the acidifying agent of composition (a) is a poly-functional organic acid.

17. The kit of claim 15, wherein the acidifying agent of composition (a) is the at least bi-functional Brønsted-acid of composition (b).

18. The kit of claim 15, wherein the acidifying agent is an inorganic acid.

19. The kit of claim 12, wherein the at least bi-functional organic acid of composition (b) is selected from the group of oxalic-, malonic-, succinic-, glutaric-, adipic-, pimeric-, suberic-, azelaic-, sebacic-, undecanedioic-, dodecanedioic-, methylmalonic-, methylsuccinic-, 2-methylglutaric-, aspartic-, maleic-, fumaric-, itaconic-, mesaconic-, methylmaleic-, phthalic-, is ophthalic-, terephthalic-, malic-, ketomalonic-, 4-ketopimelic-, citric-, isocitric-, actonitic-, propane-1,2,3-tricarboxylic-, trimesic-, methanetetracarboxylic-, ethylenetetracarboxylic-, meso-butane-1,2,3,4-tetracarboxylic-, furantetracarboxylic-acid, derivatives and mixtures thereof.

20. The kit of claim 12, wherein the compositions (a) and (b) are independently mixed into a cosmetically acceptable carrier and wherein the cosmetically acceptable carrier of the composition (a) is either identical or is not to the cosmetically acceptable carrier of the composition (b).

21. The kit of claim 15, wherein the acidifying agent is a mono-functional organic acid.

22. The kit of claim 15, wherein the alkalizing agent is an at least bi-functional Brønsted-base.

23. The kit of claim 15, wherein the alkalizing agent of composition (b) is the at least bi-functional Brønsted-base of composition (a).

24. The kit of claim 15, wherein the acidifying agent of composition (a) is the at least bi-functional Brønsted-acid of composition (b) and the alkalizing agent of composition (b) is the at least bi-functional Brønsted-base of composition (a).

25. The kit of claim 12, wherein the compositions of steps (a) and (b) are independently mixed into a cosmetically acceptable carrier and wherein the cosmetically acceptable carrier of the composition of step (a) is either identical or not to the cosmetically acceptable carrier of the composition of step (b).

26. The kit according to claim 12, wherein the at least bi-functional Brønsted-base of the general composition X—R—Y of composition (a) comprises 4,7,10-trioxa-1,13-tridecanediamine, 4,9-dioxa-1,12-dodecanediamine, 1,11-diamino-3,6,9-trioxaundecane, or a mixture thereof.

27. The kit for treating hair according to claim 12, wherein the at least bi-functional organic acid of composition (b) comprises maleic acid, itaconic acid, or a mixture thereof.

28. The kit according to claim 12 for treating hair, comprising three separate compositions (a) and (b) and (c), wherein composition (c) is a hair care conditioner.

29. The kit of claim 28, wherein the composition (a) is mixed into a commercially available hair coloring or hair bleaching formulation prior to the application to hair.

30. The kit of claim 28, wherein prior to the application of step (a) the hair is treated with a thioglycolic acid containing hair care composition.

* * * * *